United States Patent [19]

Fowler et al.

[11] Patent Number: 4,831,869
[45] Date of Patent: May 23, 1989

[54] APPARATUS AND METHODS FOR MEASURING CELL ADHESION

[76] Inventors: Harold W. Fowler, 16 Manor Road, Saltford, Bristol, England, BS18 3DM; Peter F. McCulloch, 16 Finney Drive, Wilmslow, Chesire, England, SK9 2ES

[21] Appl. No.: 63,302

[22] PCT Filed: Sep. 16, 1986

[86] PCT No.: PCT/GB86/00545
§ 371 Date: May 14, 1987
§ 102(e) Date: May 14, 1987

[87] PCT Pub. No.: WO87/01804
PCT Pub. Date: Mar. 26, 1987

[30] Foreign Application Priority Data
Sep. 17, 1985 [GB] United Kingdom ............... 8522923

[51] Int. Cl.⁴ .............................................. G01N 3/00
[52] U.S. Cl. ................................................ 73/150 A
[58] Field of Search ............. 73/865.3, 150 R, 150 A; 356/39

[56] References Cited

FOREIGN PATENT DOCUMENTS 814952 6/1953 Fed. Rep. of Germany ........ 356/39

OTHER PUBLICATIONS

Crouch et al., "The Adhesion of Animal Cells to Surfaces: The Measurement of Critical Surface Shear Stress Permitting Attachment or Causing Detachment"; J. Chem Tech. Biotechnol; pp. 273–281; Dec. 1985.

Rogers et al., "The Adhesion of Particles Undergoing an Elastic–Plastic Impact with a Surface", J. Phys. D. Appl. Phys., 17, pp. 677–689; 1984.

Primary Examiner—Stewart J. Levy
Assistant Examiner—Robert R. Raevis
Attorney, Agent, or Firm—Oldham & Oldham

[57] ABSTRACT

A method and apparatus for measuring cell adhesion with each other or with surfaces wherein a fluid containing a suspension of the cells is accelerated from a first velocity lower than a second velocity whilst flowing through a measuring chamber a surface of which constitutes a substratum to which adhesion of the cells is to be measured, and the distance along the substratum to which the cells adhere for a known initial flow rate is measured.

13 Claims, 8 Drawing Sheets

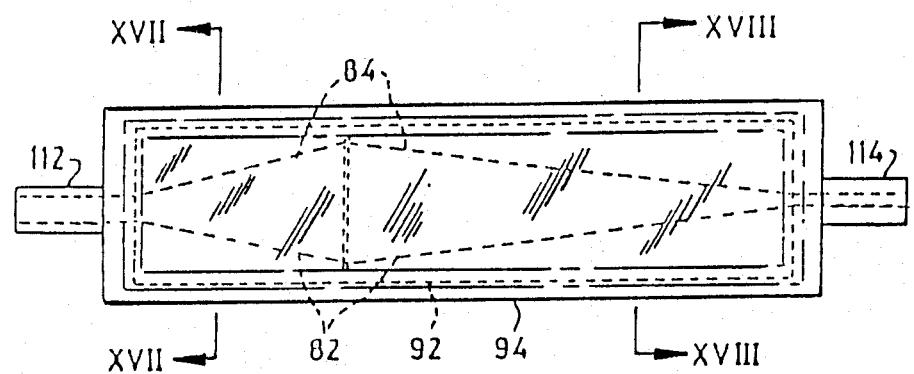
Fig 15
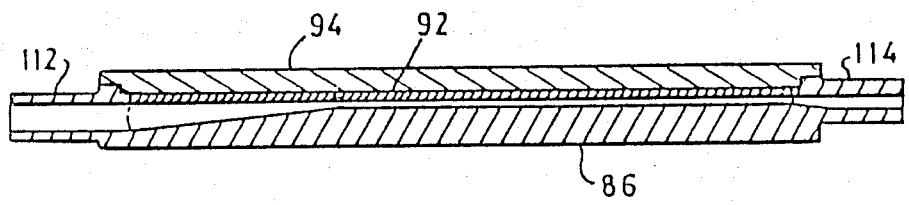
Fig.16
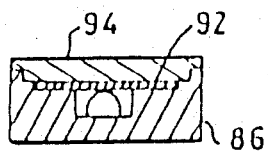 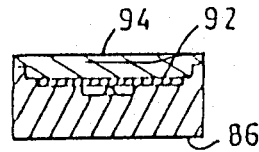
Fig.17          Fig.18

APPARATUS AND METHODS FOR MEASURING CELL ADHESION

FIELD OF INVENTION

This invention concerns apparatus and methods of measuring cell adhesion such as the forces involved in the interactions (such as attraction, attachment, adhesion, binding or detachment) of macro-molecules (such as, proteins or polysaccharides) or of cells (prokaryotic or eukaryotic) with each other or with sub-strata or surfaces (whether animate or inanimate) or any combination of the aforesaid.

BACKGROUND TO THE INVENTION

In any biological situation, there are, to a greater or lesser extent, attractive forces between molecules, cells and substrata leading to the attachment of molecules and/or cells to the substrata or to each other. Such forces give rise to effects in a wide variety of situations, some beneficial and others undesirable.

The effects may be grouped into three main areas:

1. Natural environment

Slime layers occur on rocks, in lakes, in rivers or the sea, on boats and ships, or on other submerged structures such as off-shore oil rigs. Apart from the direct effects of such layers, such as increasing the drag resistance on ships in the water, the biological fouling gives rise to other problems, such as the corrosion of surfaces beneath the layer.

2. Medical situations

The formation of dental plaque on teeth is a familiar effect and it will be obvious that there must be attachment of tissue cells to surfaces such as bone.

Likewise, the attachment of platelets from the blood stream at the site of an injury is part of the normal healing process, but the adhesion of blood cells to vessel walls or to each other leads to thrombus formation and the attendant problems.

The inflammatory response in injured tissues involves the attachment of leucocytes to the walls of the blood vessels and the passage of the leucocytes through the walls, giving rise to inflammation in the adjoining tissues.

In addition, it has been shown that normal and diseased tissue cells differ in their adhesive behaviour, while at the molecular biochemical level, the binding effects in the anitgen-antibody reactions (including the uses of monoclonal antibodies) are of particular interest in the study and understanding of immunity and the immune response.

3. Industrial situations

The attachment of cells to surfaces gives rise to costly problems in industry in the fouling of heat exchangers, cooling towers and other process equipment, as well as in pipe-lines where the increased friction due to the biological layer reduces the flow capacity of the pipe. In fermenters and biochemical reactors, growth on walls gives rise to cleaning and other problems, while if probes and sensors become covered, control of a system becomes complicated or breaks down.

Conversely, surface attachment is used as a method of immobilisation of cells in reactors, in which the trickling filter used in waste water treatment is probably the best known example, whilst the surface immobilization of animal cells enters into processes such as the manufacture of vaccines.

As might be expected, the ubiquity of the interactions between cells, molecules and substrata means that there is a common ground between situations which are, apparently, very varied. Generally, the primary attachment is a physico-chemical process, followed by a secondary biological stabilization. However, this basic mechanism of little specificity is complemented by highly specialised adhesion recognition mechanisms, making individual situations very specific. The need for a specific key to open a given lock is a useful analogy.

PRIOR ART

Methods for measuring cell adhesion have been reported in the literature and have been reviewed by H W Fowler and A J MacKay in "Microbial Adhesion to Surfaces" edited by Berkeley and others, published by Ellis Horwood in 1980. All the described methods have limitations as a general method and none has been found to be capable of wide application, but has tended to be suitable for specific situations. Since there is common ground between different systems a method capable of universal application would be desirable.

A radial flow chamber has been used in the L H Fowler cell-adhesion measurement module manufactured and supplied by L H Fermentation Limited. Such a device overcomes some of these limitations but is not ideal for all situations, particularly in studying eukaryotic cells ( which are slow growing compared with micro-organisms) and in medical studies where only small volumes of materials are usually available.

SUMMARY OF THE INVENTION

According to one aspect of the present invention a method of measuring the adhesion of cells to a substratum comprises the steps of:

(1) accelerating a fluid comprising a suspension of the cells whose adhesion to the substratum is to be measured, from a first velocity to a second velocity, whilst passing from an inlet to an outlet of a measuring chamber, at least a part of the internal wall surface of which is formed from or coated with the said substratum;

(2) measuring the rate of flow towards the measuring chamber (the said first velocity); and (3) measuring the distance from a fixed point in the measuring chamber in a direction towards the outlet thereof over which cells are deposited on the said surface in the measuring chamber, the length measurement giving a measure of the adhesion of the cells to the substratum.

According to another aspect of the invention, apparatus for measuring the adhesion factor of cells to a substratum comprises:

(1) a measuring chamber having an inlet and an outlet and an internal cross-section which is adapted to accelerate a fluid as it passes therethrough;

(2) pump means for causing fluid containing a suspension cells whose adhesion is to be measured, to circulate around a closed circuit which includes the measuring chamber; and (3) fluid flow measuring means for monitoring the rate of flow of fluid into the chamber;

wherein at least part of the internal wall surface of the measuring chamber is formed from or coated with the said substratum.

For a given flow rate, the cell adhesion factor is proportional to the distance (measured from a fixed point in the chamber towards the outlet thereof), over which cells are deposited on the substratum coated on or forming an internal wall surface thereof, during the passage of the fluid therethrough.

According to a further aspect of the invention a method of measuring adhesion of cells to a substratum comprises the steps of:

(1) Accelerating a fluid from a first velocity to a second velocity whilst passing from an inlet to an outlet of a measuring chamber, at least a part of the internal wall surface of which is formed from or coated with the said substratum, and is at the outset coated with the cells;

(2) measuring the rate of flow towards the measuring chamber (the said first velocity); and (3) after a period of time measuring the distance from a fixed point in the measuring chamber in a direction towards the outlet thereof over which cells remain on the said substratum in the measuring chamber after the passage of the fluid therethrough, the distance measurement giving a measure of the adhesion of the cells to the substratum.

According to a still further aspect of the invention, apparatus for measuring the adhesion factor of cells to a given material comprises:

(1) a measuring chamber having an inlet and an outlet and an internal cross-section which is adapted to accelerate a fluid as it passes therethrough;

(2) pump means for causing fluid to circulate around a closed circuit which includes the measuring chamber; and (3) fluid flow measuring means for monitoring the rate of flow of fluid into the chamber, wherein at least part of the internal wall surface of the measuring chamber is formed from or coated with the said substratum.

For a given flow rate, the cell adhesion factor is proportional to the distance (measured from a fixed point in the chamber towards the outlet thereof), over which cells remain on the said internal wall surface thereof after the fluid has passed therethrough.

Preferably there is also provided input means by which cells and/or fluid can be introduced into the said closed circuit.

Preferably drainage means is also provided through which the contents of the closed circuit can be flushed.

Preferably the measuring chamber is of rectangular cross-section and either one or both of the opposed pair of parallel internal faces of the chamber are formed from or coated with the substratum whose adhesion to the cells under test is to be measured, and either a layer of the cells is then applied to the said surface before a fluid flow is induced or fluid containing a suspension of the cells is then pumped through the chamber in the manner as aforesaid.

Preferably one of the pairs of opposed parallel internal faces are spaced apart by a gap of the order of 1 mm to 2 mm.

Preferably the side walls of the chamber converge towards the exit so that the cross-section of the chamber reduces in width from a slit of typically 20 mm×1 mm to an exit slit of typically 3 mm×1 mm.

Preferably the feed to the measuring chamber is itself a slit like passage the cross-section of which changes in shape but remains constant in area from a fluid pipe connection to a slit like entrance to the measuring chamber, so that whilst there is a change in the flow pattern there is no increase in velocity of the fluid as it passes from a supply pipe to the measuring chamber entrance.

Apparatus embodying the invention is readily adapted to be used with a relatively small volume of fluid and is therefore capable of being used in medical and other fields where the available volume of a cell sample may be very small.

Conveniently one or more of the parallel walls of the measuring chamber may be in the form of a microscope slide, which may be preconditioned if required.

The measuring chamber may be supplied as a sterilized disposable unit to avoid the need for sterilization.

Inspection of the extent to which cells cover the surface or surfaces of the parallel walls of the measuring chamber, may be made visually and a record made for subsequent analysis, or may be performed using imaging techniques, whereby the chamber wall may be imaged and the image analyzed using an image analyzer which may be computer controlled and/or may incorporate a computer, the results of the analysis being displayed for observation and recordal by the observer and/or stored in a memory associated with the analyzer.

The principal relied on by the measuring system so far described is that as a cell suspension is accelerated over a substratum (or a liquid is accelerated over a layer of cells on a surface) a critical speed is finally achieved at which the shear surface stresses reach a value such that cells in suspension are prevented from adhering to the surface (or those clinging to the surface are stripped away).

Thus if a fluid containing cells in suspension is accelerated from a velocity below to a velocity above this critical velocity, after a period of time, cells will be found to have adhered to that part of the surface over which the suspension passes at speeds which are less than the critical velocity, but not beyond.

Likewise if a fluid is accelerated from the lower to the higher velocity whilst in contact with a layer of cells already adhering to the said surface, cells will be found to have been stripped from that part of the surface over which the fluid is moving at speeds greater than the critical velocity and visa-versa.

If the initial velocity and the acceleration are constant, then the length of the surface over which the cells are deposited (or left adhering) will vary in dependence on the strength of the adhesive bond between the cells and the surface. The latter can thus, for example, be calibrated so that the adhesion of cells to the surface can be measured by direct observation or by automated analysis of the length of the measuring chamber over which cells are found after the flow of fluid through the chamber.

Where one or more internal surfaces of the chamber are to be coated with a layer of cells before a test in which a fluid is flowed through the chamber so as to cause some of the cells to be stripped away, the cells are most simply introduced into the chamber by introducing a first fluid containing the cells in suspension into the chamber, so that the cells will be deposited as a thin layer onto the internal surface(s) of the chamber. After sufficient cells have been laid down in this way, the chamber can be rinsed using a slow flowing wash to remove all traces of the first fluid containing the cells in suspension, whereafter the proper test can be conducted using a higher velocity flow of the liquid used for the rinse or another special purpose liquid.

The first fluid (containing the cells) may be introduced into the chamber by using a hypodermic type syringe to inject the suspension into the inlet or outlet of the chamber, which can then if desired be sealed and lightly agitated or centrifuged or simply left for a period of time, so as to cause the cells to become coated on the interior of the chamber.

If it is preferred to leave the chamber in place and deposit the cells with minimal interference to the fluid connections to the chamber, a side port may be provided either in the chamber or in a connection leading to the chamber, so that the cell suspension can be injected into the closed loop, which is typically filled with a fluid buffer, and the cells can be deposited by gently circulating the buffer solution containing the cells in suspension until the surfaces have been fully coated, after which it is a simple matter to either increase the flow rate through the chamber to perform the test using the buffer or drain out the buffer and replace it with the fluid to be used during the test.

The invention will now be described, by way of example, with reference to the accompanying drawings, in which.

Figure 6:
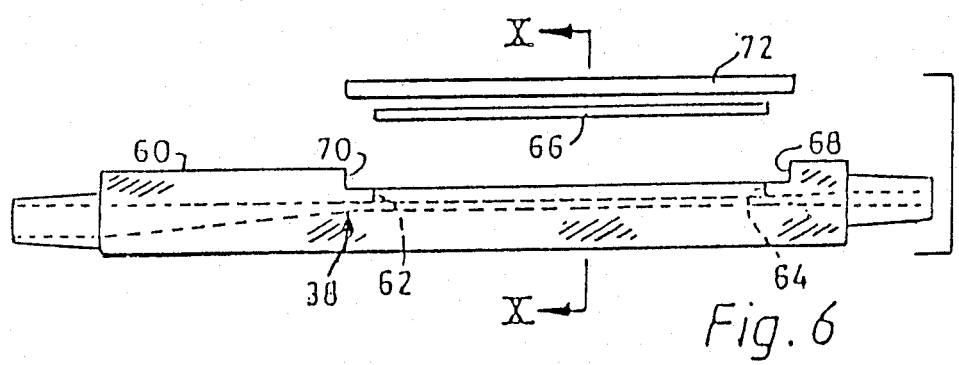
Figure 7:
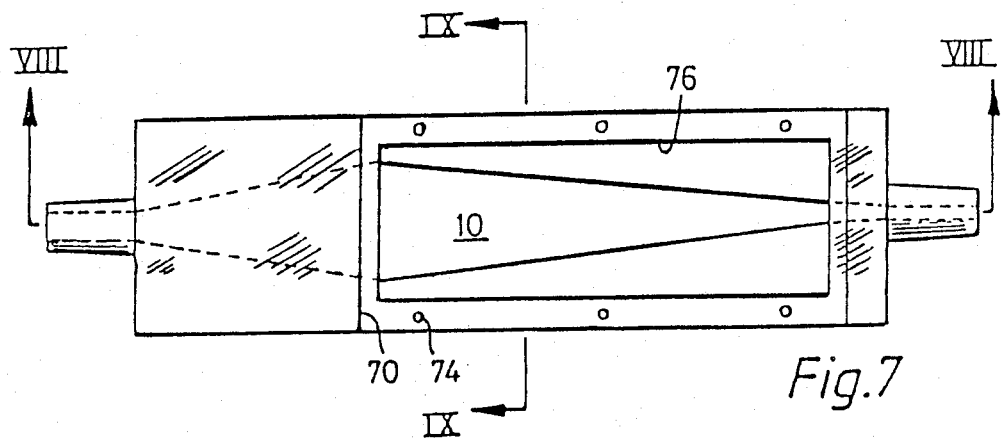
Figure 8:
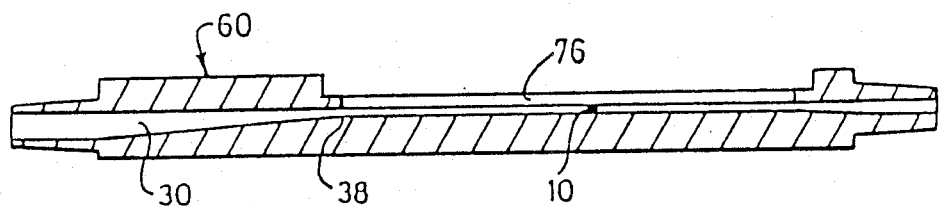
Figure 9:
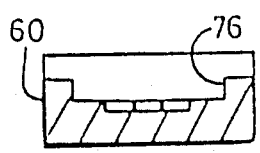
Figure 10:
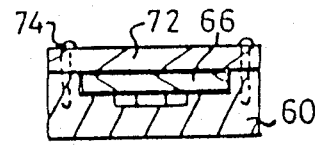
Figure 11:
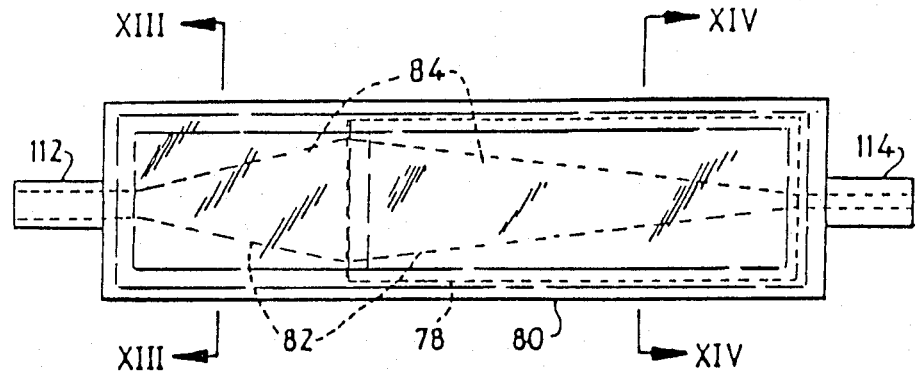
Figure 12:
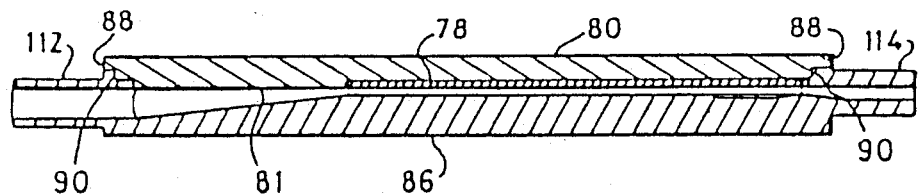
Figure 13:
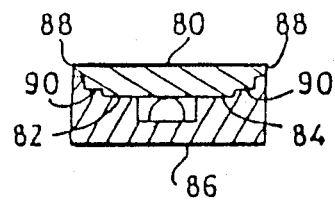
Figure 14:
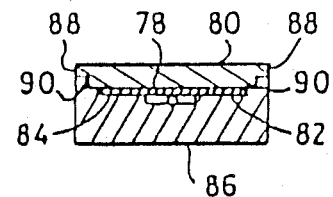
Figure 19:
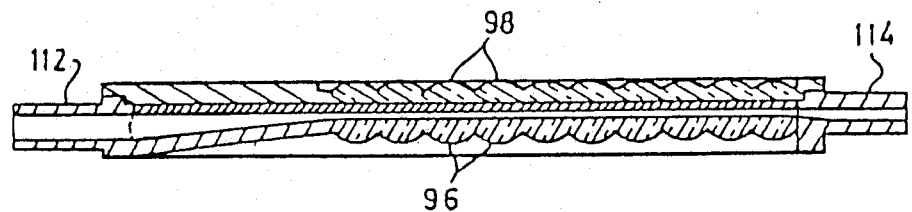
Figure 20:
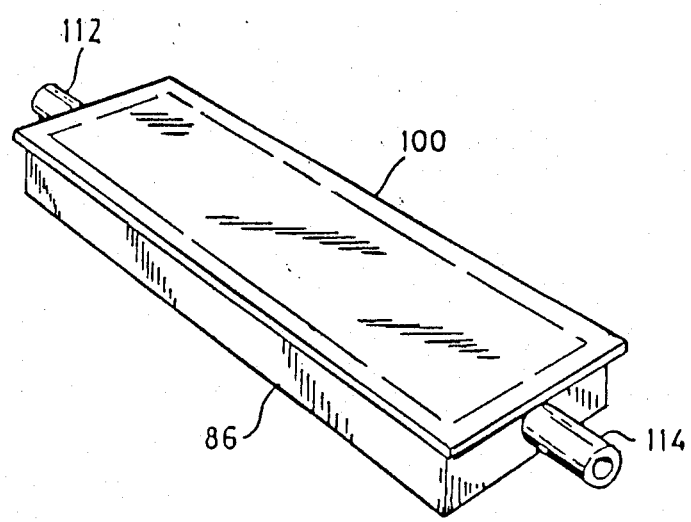
Figure 21:
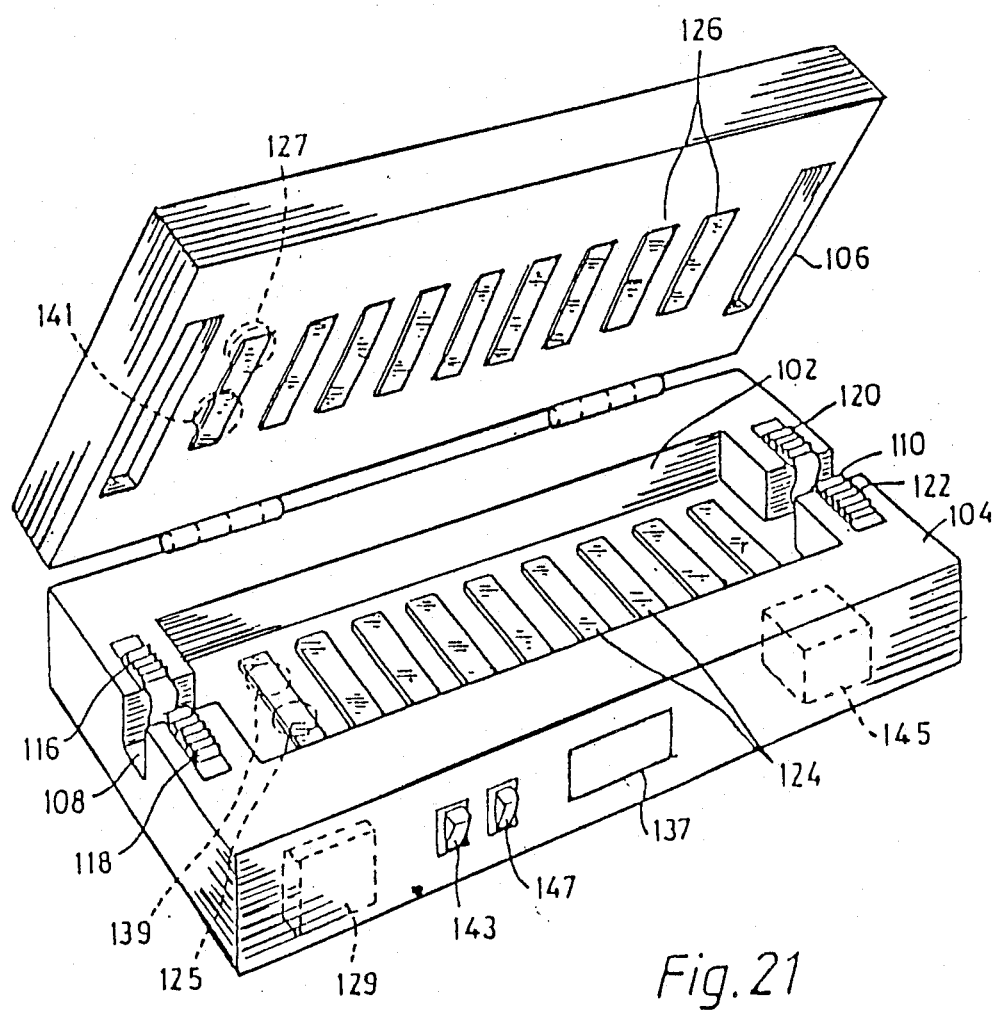
Figure 22:
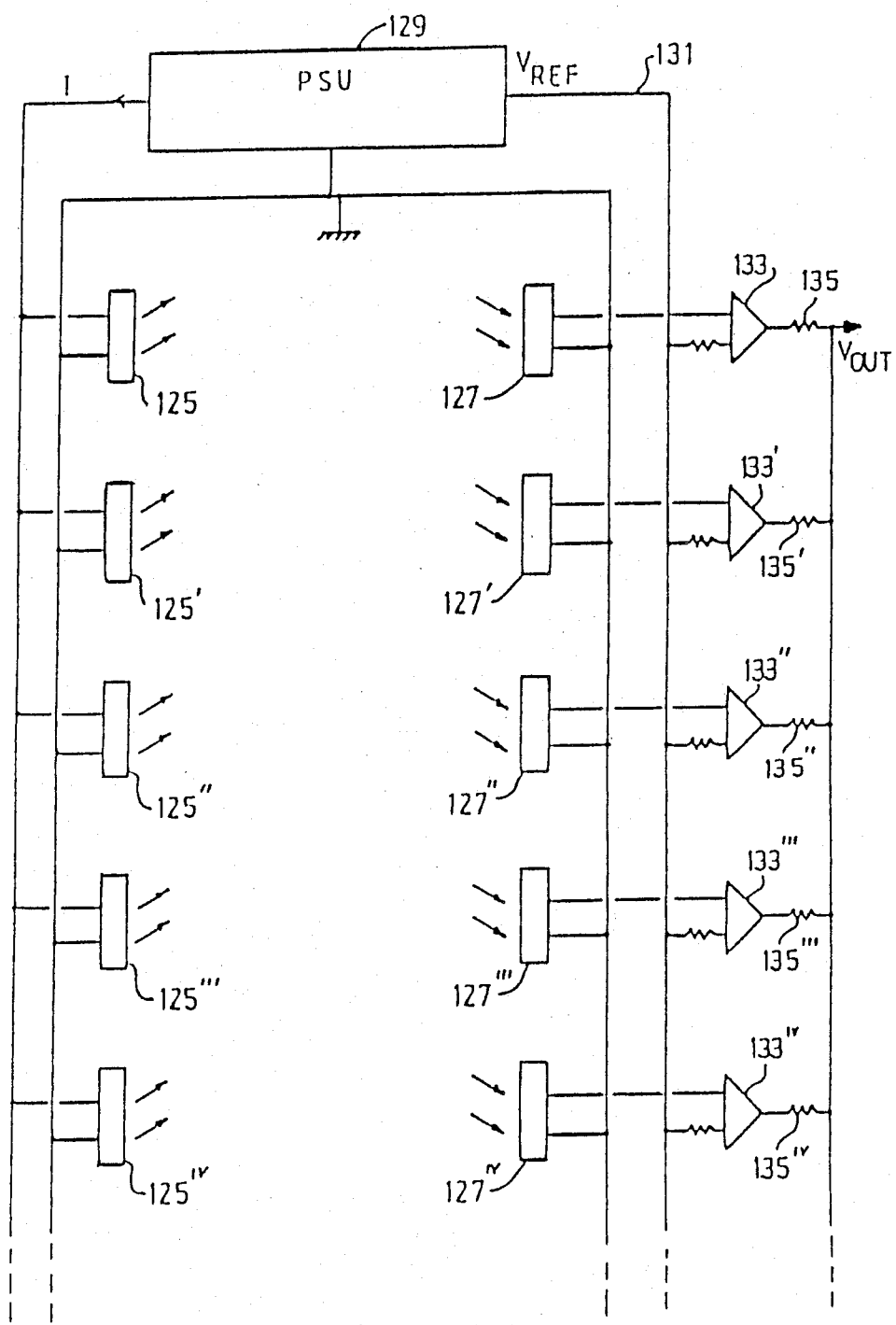

FIG. 6 is a side view of a modified device in which part of the wall of the measuring chamber is removable and is shown removed in FIG. 6, FIG. 7 is a plan view of the device of FIG. 6 with the removable wall section and cover-plate removed, FIG. 8 is a cross-section on the line VIII—VIII of FIG. 7, FIG. 9 is a cross-section on the line IX—IX of FIG. 7, FIG. 10 is a cross-section through the assembled unit of FIG. 6 on the line X—X, FIGS. 11-14 are a set of views similar to FIGS. 7-10 of another form of construction of measuring chamber, for use in the method of the invention;

FIGS. 15-18 are a further set of views similar to FIGS. 7-10 of a further form of construction of measuring chamber for use in the method of the invention;

FIG. 19 is a cross-section through a modified form of the measuring chamber shown in FIGS. 15-18;

FIG. 20 illustrates in a perspective view a measuring chamber such as shown hitherto but to which the cover is adapted to be fitted or removed more readily;

FIG. 21 is a perspective view of a desk-top unit adapted to receive a measuring chamber such as shown hitherto for automatic viewing and analysis, and FIG. 22 is a schematic circuit diagram of one arrangement for generating an output signal indicative of the cells remaining after a test.

DETAILED DESCRIPTION OF THE DRAWINGS

Figure 1:
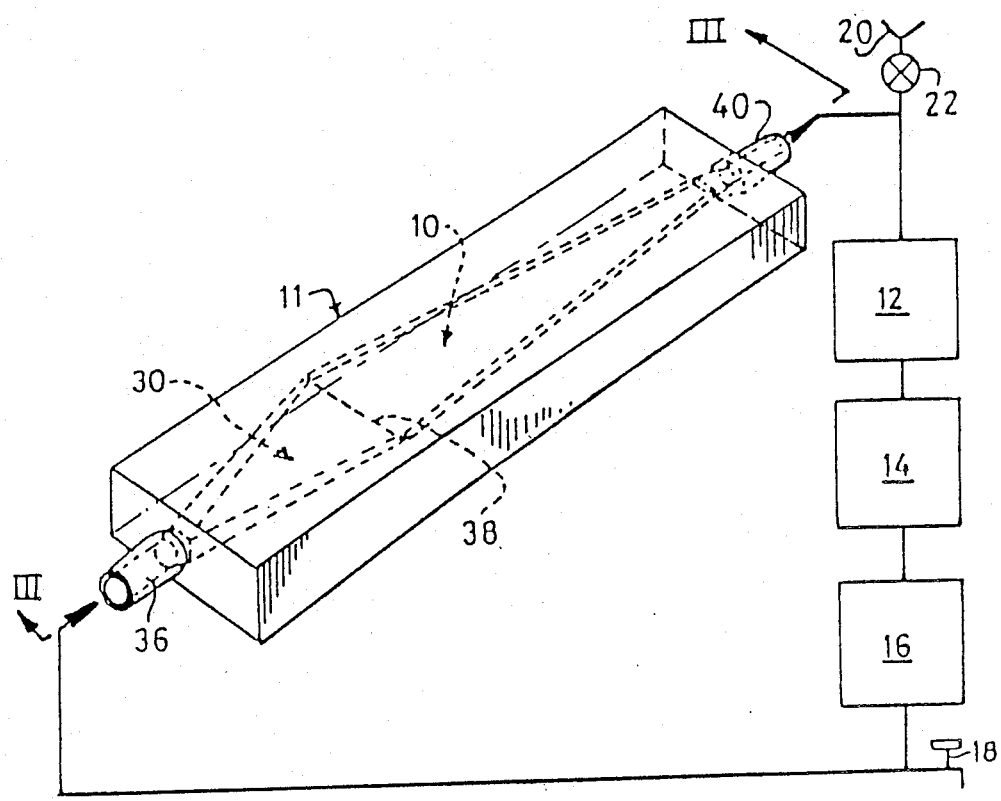
FIG. 1 is a diagrammatic view of apparatus embodying the invention.

As shown in FIG. 1 a flow measuring chamber 10 in a housing 11 is connected in a closed loop by means of pipework (not shown) which includes a reservoir 12, a pump 14 and a flow meter 16. A tap 18 allows the system to be drained of fluid and flushed and an inlet in the form of a funnel 20 and control valve 22 (or similar device) is provided to allow fluid to be introduced into the circuit. The measuring chamber 10 is generally trapezaidal in shape when viewed in plan but is a narrow slit when viewed from the side. This is best seen by comparing FIGS. 2 and 3.

The upper and lower inside surfaces 24 and 26 of the measuring chamber coated with or formed from the test material or substratum, the adhesion of certain cells to which is to be measured. Flow between the two surfaces is arranged to be uniform by providing a lead-in section 30 of generally rectangular cross-section in which all four walls diverge towards the entrance slit to the measuring chamber 10 and in which the area of the cross-section is substantially constant from the inlet connection 36 to the ridge 38 defining the entrance of the measuring chamber 10.

Typically the inlet connection 36 to which the pipework from the pump and flow meter can be connected has an internal diameter of 5 mm. Over a distance of approximately 40 mm the circular inlet 36 changes to a rectangular section slit some 20 mm×1 mm and since the area of the 5 mm diameter inlet pipe and the 20 mm×1 mm slit are approximately the same, the fluid will have the same velocity at the exit or at the entrance to the lead in section 30.

The spacing between the faces 24 and 26 in the measuring chamber 10 is 1 mm and the width tapers from the 20 mm at the ridge 38 (the inlet) to 3 mm at the outlet. The taper is uniform and extends over a distance of approximately 76 mm from the ridge 38 to the final rectangular section of 3 mm×1 mm.

The outlet connection 40 has an internal passage which changes shape from the 3 mm ×1 mm section at the end of the measuring chamber 10 to a 2 mm internal diameter passage in a sleeve 40 to connecting to pipework (not shown) for conveying fluid to the reservoir 12 and punp 14.

The converging and reducing cross-section of the measuring chamber 10 causes the fluid flowing through the chamber to increase in velocity as it passes therethrough, giving rise to increasing surface shear stresses. Where the liquid contains cells in suspension, the latter will only be deposited on and adhere to surfaces such as 24 or 26 where the flow rate is below the critical speed at which the surface shear forces are too great to allow adhesion to occur.

Where the cells are deposited at the outset on the surfaces such as 24 or 26, and a liquid is then passed through the chamber, the cells will only be able to remain on that area of either surface over which the flow rate is less than the said critical speed.

Thus measuring from the ridge 38 in the direction of the outlet 40, the distance over which cells are deposited (or remain adhering to the surface 26 or 24) gives a measure of the adhesion bond between the cells and the surface material.

The reservoir 12 serves to even out the flow which due to friction within the chamber 10 could cause the pump 14 to become starved.

Flow meter 16 accurately measures the rate of flow of the liquid into the input end 36 of the unit and typically the pump output is adjustable to ensure that a constant rate of flow is maintained.

Figure 2:
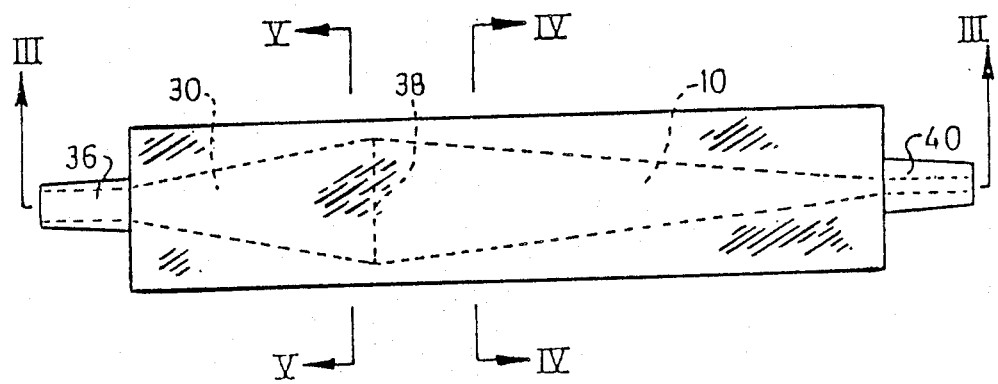
FIG. 2 is a plan view of the measuring chamber.
Figure 3:
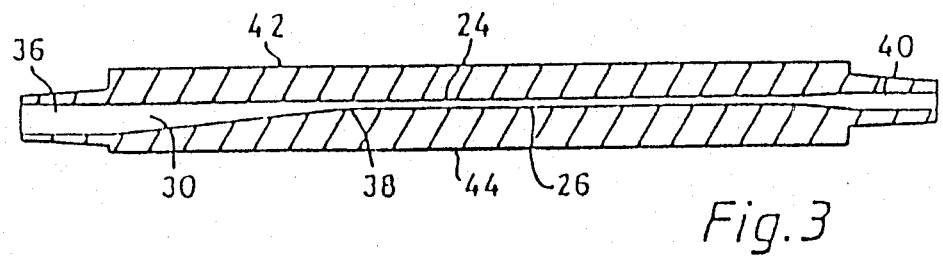
FIG. 3 is a cross-section on line III—III in FIG. 2.

FIG. 3 already referred to shows the cross-section of the passage through the housing and by comparison with FIG. 2 illustrates how the cross-sectional shape of the passage through the unit changes from the inlet 36 to the outlet 40.

The housing 11 may be formed from glass or metal or plastics material or any combination thereof. Preferably however the unit is formed from injection moulded plastics material and most conveniently is formed in two halves which are then bonded to form the final unit.

By forming at least part of the upper or lower (or both) walls 42, 44 from transparent material or by providing windows in at least one or the other of these walls, measurement of the extent of cell deposition (or adherence) can be made by direct observation or by forming an image of what can be seen through the window (or windows) and analyzing same, using an image analyzing computer or the like (not shown).

Figure 4:
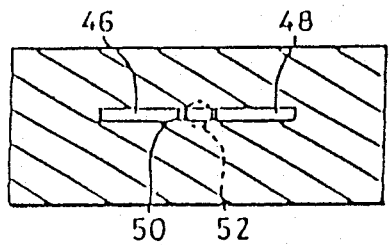
FIG. 4 is a cross-section on the line IV—IV in FIG. 2.
Figure 5:
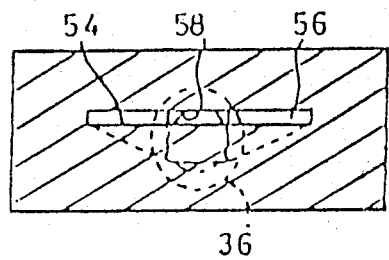
FIG. 5 is a cross-section on the line V—V in FIG. 2.

FIGS. 4 and 5 further illustrate the cross-sectional shape of the various parts of the passage through the unit, the view of FIG. 4 showing how the side walls 46 and 48 of the measuring chamber converge towards the rectangular outlet slit 50 the dimensions of which are 1 mm×3 mm. By way of hidden detail the section also shows how the rectangular exit slit 50 becomes a circular outlet passage 52 having a diameter of approximately 2 mm.

The cross-section of FIG. 5 shows the converging side walls 54 and 56 of the lead in section 30 and, partly by way of hidden detail, illustrates the entrance passage 58 having an internal diameter of 5mm through the inlet connection 36.

Advantageously at least one of the test surfaces 24 or 26 in the measuring chamber 10 comprises a standard 3"×1". microscope slide. Not only does this provide a readily available optically flat surface but these will also fit standard culture and storage systems. Thus the embodiment of the invention shown in FIG. 6 is a modification of the device previously illustrated, which enables a microscope slide to form one of the walls of the measuring chamber.

Referring to FIG. 6, the unit is formed from a main body section 60 similar to the unit shown in FIGS. 1 to 3 but having a recess denoted by dotted lines 62 and 64 in FIG. 6 into which a microscope slide 66 can be dropped and a rebate above the recess having end walls 68 and 70, into which a coverplate 72 can be fitted. The latter is conveniently secured in place by means of pins, rivets or screws and to this end, six fixings 74 are shown in FIG. 7.

FIG. 7 more clearly illustrates the recess 76 into which the microscope slide 66 can fit and further demonstrates the platform around the recess on which the coverplate 72 sits.

Further detail of the recess 76 can be seen from the cross-section of FIG. 8 and by a comparison of the Figure with the cross-section of FIG. 9 and the cross-section through the assembled unit shown in FIG. 10.

FIGS. 11–14 illustrate a chamber in which a glass microscope slide 78 is held in place by a cover plate 80 of clear plastics material, the latter being formed with a shallow stepped section 81 to hold the slide in place. The depth of step 81 is just made equal to the thickness of the slide so that the underside of the combination is smooth and flat and can rest on the two parallel side cheeks 82, 84 of the base 86. The width of the slide 78 and the stepped section 81 of the underside of the coverplate 80 is less than the width of the coverplate, and the peripheral region of the coverplate is itself stepped to provide an outer, thin flange 88 so as to fit into a peripheral rebate 90 in the base 86.

The slide 78 can be sealed and the cover 80 secured in place by, for example, a layer of adhesive sealant between the step in the cover and the peripheral rebate 90 in the base. Alternatively in another example, double sided adhesive tape may be fitted between the step and the peripheral rebate 90.

In FIG. 15–18 an alternative design is shown in which a longer glass slide 92 is employed, the length of which is sufficient to cover both the converging and diverging regions of the chamber, thereby obviating the need for a step in the underside of the coverplate 94, as in FIGS. 11–14. In all other respects the design is similar to that of FIGS. 11–14 and similar reference numerals have been employed and reference should be made to the description of FIGS. 11–14 for a description of these items.

Where an estimate of the extent of cellular coverage is required, the slide 92, may be illuminated for example, from below, and viewed from above. To assist in this estimation a series of cylindrical condensing lenses 96 may be formed as by moulding, in the underside of the base and a corresponding series of cylindrical lenses 98 may be formed as by moulding in the upper surface of the cover plate 94, as shown in FIG. 19.

This technique may be applied to any of the arrangements shown in FIGS. 7–18.

Where the cover plate 94 is to be filled by an operator using protective clothing or in the dark, it is advantageous for the upper peripheral region (88 in FIGS. 11–14) to extend beyond the edge of the base 86, to facilitate handling. To this end the cover plate may be formed with an oversize lip 100, as shown in FIG. 20.

The oversize cover plate may be fitted to either of the arrangements shown in FIGS. 11–14 and FIGS. 15–18. If this feature is required in the FIGS. 7–10 arrangement, only the width of the cover plate 72 can be increased beyond that shown.

Where automated inspection and analysis is to be undertaken the test chamber is conveniently supported in a recess 102 in the base 104 of an inspection unit, having a hinged lid 106. Slots 108, 110 at opposite ends of the recess 102 allow the inlet and outlet pipe connections such as 112, 114 in FIGS. 11–18 to extend externally of the base for connection to flexible pipes (not shown) for completing the fluid circuit. Spring loaded jaws 116, 118 and 120, 122 serve to grip the connections 112, 114 and hold the measuring chamber assembly of base and cover plate in place.

The base of the recess 102 includes a plurality of windows such as 124 through which light can pass from bulbs or light emitting diodes such as 125 located therebelow.

The underside of the lid 106 is likewise formed with a corresponding plurality of windows 126 through which the illuminated regions of the measuring chamber can be viewed by light sensitive devices, such as 127, are behind each window.

Power supply means 129 is located in the base for supplying electric current to the light sources below the windows 124 and the light sensors behind the windows 126 and to circuit means (see FIG. 24) responsive to the outputs from the sensors to produce an electrical signal having a parameter (such as voltage or current) which is proportional to the number of sensors 127 which receive a full complement of the light output from their respective light sources 125. By arranging that the layer of cells sufficiently blocks off the passage of light as to restrict the output signal level from the sensors 127, so the magnitude of the said parameter can be measured at the beginning of the test when either all of the light paths will be blocked (due to a layer of cells on the slide at the outset of the text), or more will be blocked (where the cells are to be deposited during the test), and again at the end of the test (when only some of the length of the slide will have cells adhering thereto). The difference between the two measured parameter values will give a measure of the length of the slide from which cells have been removed (or have failed to gain a footing) -depending on the nature of the test.

Preferably the output from each sensor is converted into binary form before being combined with the other sensor outputs, as by comparing the sensor output with a reference 131 in a differential amplifier 133 and generating one output signal condition if the reference is exceeded and a second output signal condition if the output signal fails to reach the reference.

By connecting the outputs of all the differential amplifiers 133, 133' etc to a common point via summing resistor 135, 135', etc so the output current will be proportional to the number of sensors 127, 127' etc, which are sufficiently illuminated (due to the absence of cells) as to produce output voltages which exceed V ref (131) and thereby switch on their respective ammplifiers 133, 133' etc.

The unit may include a display 137 for indicating digitally (or in an analogue manner using a moving coil meter) the value of the output signal V out.

Additional light sources such as 139 may be provided below and/or above as at 141, to provide illumination of the measuring chamber when in situ and may generate visible or infra red of ultra violet radiation. A switch 143 is provided to control and select such illumination.

When closed the lid preferably prevents light from entering the inspection unit housing.

The interior of the inspection unit housing may be temperature controlled and may to this end include a heating or cooling element 145 or both, to enable the internal environment of the unit to be controlled at least for the duration of a test. A switch 147 controls the heater or cooling unit 145.

Reference to light herein is intended to include ultra violet and infra red as well as radiation in the visible spectrum.

Where it is desirable to be able to evaluate the effect on cell adhesion of ultra violet or infra red radiation, or visible light, the sources (such as 139, 141) can be selected as appropriate, for irradiating the chamber during a test.

GENERAL

Tests have shown that for microbial cells, the attachment and detachment forces are substantially the same. However in the case of animal cells, these forces may differ by several orders of magnitude. Adhesion of animal cells can also be considerably affected by the pH as well as the source, and concentration, of the serum.

Reference has been made to earlier devices for adhesion measurement such as the LH Fowler Cell Adhesion Measurement Module supplied by LH Engineering Co. Ltd. of Stoke Poges, Buckinghamshire. In this earlier instrument the fluid suspension of cells enters a flat circular chamber in the center and is radially distributed. Cell deposition occurs as the fluid speed reduces with distance from the center. One of the objectives of the present invention was to reduce the volume of fluid needed for performing such measurements and superficially it would appear that one way to reduce the volume of liquid in a radial flow system would be to take a sector representing 10% or 15% of the circular chamber and obtain a similar range of decreasing shear forces in a divergent channel so obtained.

However from experimental work and using theoretical model it has been discovered that this is not possible. Hydrodynamic theory indicates that boundary layer separation takes place in a divergent channel and in fact there can be a complete reversal of the direction of the flow close to the walls of such a channel which is of course the area of interest in the context of a cell measuring system. It has been discovered that no such separation occurs in a convergent channel and in such a channel the flow has been found to remain stable. Indeed the phenomenon known as relaminarization has been observed. Such that even if there is some degree of turbulence at the entrance to the convergant channel, laminar flow is quickly attained and is maintained (provided the channel parameters are correct) even at velocities showing Reynolds Numbers where turbulance would be expected.

Thus in a device embodying the present invention the lowest shear forces are experienced at the inlet of the chamber and increase through the chamber to the outlet whereas the opposite is the case in a radial chamber.

Apart from the hydrodynamic advantages associated with relaminarization in a convergent channel, there is also a biological advantage. On a number of occasions when using the radial chamber such as the LH Fowler instrument referred to above, with a confluent layer of cells, it was observed that the higher shear forces near the inlet could lift the edge of a sheet of cells and remove a large area of cells in one piece. No such occurence has been observed in a convergent channel and a comparison of the radial-divergent channel versus the convergent channel indicates that the latter has a higher critical shear force before detachment occurs.

Wherein sterilization and aseptic operation are important considerations, a pump having a magnetic drive is advantageous. However removal of air from the system can be a problem and a peristaltic pump may alternatively be used.

The converging measuring chamber provides a restriction which increases the pressure drop and reduces the pulsations produced by the pump. These can be eliminated by use of damping changes such as the reservoir in the embodiment shown in the drawings.

SUMMARY OF EXPERIMENTAL RESULTS

Experiments have been confined to the use of baby hamster kidney cells (BHK21C-13 from Flow Laboratories Ltd). These are a recognized line, known to be anchorage-dependent and have enabled the results to be compared with similar results obtained using earlier cell adhesion measuring instruments.

For the purpose of these experiments, apparatus similar to that shown in FIGS. 6 to 10 of the drawings was used and in each case the glass microscope slide was coated with the cells and after the detachment run, was removed, and the remaining cells were fixed and stained with Coomassie Blue and examined microscopically to determine the critical length.

Typical results obtained using such apparatus are set out in the Table I below. In this Table all the tests were based on running the medium through the cell for 20 minutes at 21° C.

Comparison of the values in the Table for the critical shear forces shows acceptable consistency at the prototype development stage. Furthermore good agreement has been obtained with results from earlier work using radial flow measuring instruments, where there is direct comparison. In such cases, the critical shear measured using an instrument embodying the present invention appear to be somewhat higher as compared with the results obtained from radial chamber apparatus and the reason for this is believed to depend on the opposite flow directions in the two systems. Thus in the earlier radial device, the shear forces start high and decrease but the reverse obtains in the apparatus of the present invention. Thus in the radial flow systems, the edge of a confluent sheet can be lifted and pulled away at a lower value than would be obtained directly. Where the cells are not confluent, so that individual cells are detached, there is good agreement.

The influence of the confluence of the cells emphasizes the need for establishing a closely defined pre-test procedure in growing and attaching cells to the slide. Thus the age of the cells and the level of the inoculation can have a significant effect. For example it is important to ensure that the same depth of fluid is used in a Petri dish in which the cell deposition process, so that consistent results are obtained.

It has also been noted that substitution of one running medium (fluid) for another has significant effects on the results obtained. Thus the use of a saline solution instead of the full culture medium halved the critical shear force. This can be seen by comparing the results of runs 7/275 and 9/275.

TABLE 1

| Ref. | Age of cells (h) | Estimated confluence (%) | Flow rate (cm/s) | Running medium | Critical length (cm) | Critical velocity (cm/s) | Critical shear ($N/m^2$) |
| --- | --- | --- | --- | --- | --- | --- | --- |
| 1/076 | 14 | 15 | 10.8 | Medium | 3.5 | 104 | 2.3 |
| 1/066 | 48 | 50 | 11.2 | Medium | 6.0 | 185 | 4.2 |
| 4/066 | 48 | 50 | 11.2 | Medium | 6.8 | 210 | 5.' |
| 1/285 | 36 | 70 | 16.7 | Medium | 2.5 | 11.5 | 2.6 |
| 3/275 | 72 | 100 | 8.7 | Medium | 7.6+ | 272+ | 4.1+ |
| 5/275 | 72 | 100 | 13.0 | Medium | 7.6+ | 406+ | 6.1+ |
| 6/275 | 72 | 100 | 15.0 | Medium | 7.6+ | 469+ | 7.0+ |
| 7/275 | 72 | 100 | 20.0 | Medium | 7.0 | 575 | 8.6 |
| 9/275 | 72 | 100 | 10.0 | Saline | 6.5 | 267 | 4.0 |
| 8/275 | 72 | 100 | 23.3 | Saline | 4.0 | 383 | 5.7 |

We claim:

1. A method of measuring the adhesion of cells to a substratum comprising the steps of:
   (1) accelerating a fluid comprising a suspension of the cells whose adhesion to the substratum is to be measured, from a first velocity to a higher second velocity, whilst passing from an inlet to an outlet of a measuring chamber, at least a part of the internal wall surface of which is formed from or coated with the said substratum;
   (2) measuring the rate of flow towards the measuring chamber (the said first velocity); and
   (3) measuring the distance from a fixed point in the measuring chamber in the direction towards the outlet thereof over which cells are deposited on the said substratum in the measuring chamber, the length measurement giving a measure of the adhesion of the cells to the substratum.

2. A method of measuring the adhesion of cells to a substratum comprising the steps of:
   (1) accelerating a fluid from a first velocity less than a second higher velocity whilst passing from an inlet to an outlet of a measuring chamber, at least a part of the internal wall surface of which is formed from or coated with the said substratum and is at the outset coated with the cells over said substratum;
   (2) measuring the rate of fluid flow toward the measuring chamber (the said first velocity); and
   (3) after a period of time measuring the distance from a fixed point in the measuring chamber in a direction towards the outlet thereof over which cells remain on the said surface in the measuring chamber after the passage of fluid therethrough, the distance measurement giving a measure of the adhesion of the cells to the substratum.

3. Apparatus for measuring the adhesion factor of cells to a substratum comprising:
   (1) a measuring chamber having an inlet and an outlet and an internal cross-section which is adapted to accelerate a fluid from a first velocity to a second higher velocity as it passes therethrough;
   (2) pump means for causing fluid to circulate around a closed circuit which includes the measuring chamber; and
   (3) fluid flow measuring means for monitoring the rate of flow of fluid into the chamber, wherein at least part of the internal wall surface of the measuring chamber is formed from or coated with the said substratum.

4. Apparatus as claimed in claim 3, wherein the measuring chamber is of rectangular cross-section and either one or both of the opposed pair of parallel internal faces of the chamber are formed from or coated with a substratum whose adhesion to the cells under test is to be measured.

5. Apparatus as claimed in claim 4, wherein one or more of the parallel walls of the measuring chamber is in the form of a microscope slide, one face of which constitutes the internal face of the chamber which is coated.

6. Apparatus as claimed in claim 4, wherein a wall of the chamber in which cells remain after the test is calibrated so that measurement of cell adhesion can be made by direct observation.

7. Apparatus as claimed in claim 4, wherein lenses are formed in a wall of the measuring chamber.

8. Apparatus as claimed in claim 4, further comprising a housing into which the measuring chamber can be fitted at least during a cell adhesion measurement, and one or more light sources are located in the housing on one side of the chamber and one or more light sensitive devices are mounted in the housing on the other side of the chamber to enable a measure of the distance over which cells adhere to an internal chamber face to be obtained automatically.

9. Apparatus as claimed in claim 8, wherein the housing is substantially light tight when closed.

10. Apparatus as claimed in claim 9, wherein means is provided for controlling the temperature within the housing.

11. Apparatus as claimed in claim 4, in which one of the pairs of opposed parallel internal faces are spaced apart by a gap of the order of 1 mm to 2 mm

12. Apparatus as claimed in claim 4, in which the faces of the side walls of the chamber converge towards the exit so that the cross-section of the chamber reduced in width from a slit of the order of 20 mm×1 mm to an exit slit of the order of 3 mm×1 mm.

13. Apparatus for measuring the adhesion factor of cells to a substratum comprising:

(1) a measuring chamber having an inlet and an outlet and an internal cross-section which is adapted to accelerate a fluid from a first velocity to a second higher velocity as it passes therethrough;

(2) pump means for causing fluid to circulate around a closed circuit which includes the measuring chamber; and (3) fluid flow measuring means for monitoring the rate of flow of fluid into the chamber, wherein at least part of the internal wall surface of the measuring chamber is formed from or coated with said substratum and, wherein a feed to the inlet of the measuring chamber is itself a slit-like passage the cross-section of which changes in shape but remains constant in area from a fluid pipe connection to a slit-like inlet to the measuring chamber, so that whilst there is a change in the flow pattern there is no increase in velocity of the fluid as it passes from a supply pipe to the measuring chamber inlet.

* * * * *